(12) United States Patent
Kuhn et al.

(10) Patent No.: US 8,428,689 B2
(45) Date of Patent: Apr. 23, 2013

(54) IMAGE GUIDED THERAPY

(75) Inventors: Michael Harald Kuhn, Hamburg (DE); Julius Cohen, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 588 days.

(21) Appl. No.: 12/602,795

(22) PCT Filed: Jun. 4, 2008

(86) PCT No.: PCT/IB2008/052178
§ 371 (c)(1),
(2), (4) Date: Dec. 3, 2009

(87) PCT Pub. No.: WO2008/152542
PCT Pub. Date: Dec. 18, 2008

(65) Prior Publication Data
US 2010/0179414 A1    Jul. 15, 2010

(51) Int. Cl.
*A61B 5/00* (2006.01)
(52) U.S. Cl.
USPC ............... 600/411; 600/412; 600/410; 601/2
(58) Field of Classification Search .......... 600/407, 600/410, 411, 412, 414, 424, 425, 426; 601/2
See application file for complete search history.

(56) References Cited

U.S. PATENT DOCUMENTS

| | | | |
|---|---|---|---|
| 5,897,495 A | 4/1999 | Aida et al. | |
| 2003/0075687 A1 | 4/2003 | Suzuki et al. | |
| 2003/0203490 A1 | 10/2003 | Vuong | |
| 2005/0121782 A1 | 6/2005 | Nakamura et al. | |
| 2006/0002632 A1 | 1/2006 | Fu et al. | |
| 2006/0074292 A1 | 4/2006 | Thomson et al. | |
| 2007/0043286 A1 | 2/2007 | Lu et al. | |
| 2010/0094128 A1* | 4/2010 | Manzke et al. | 600/426 |
| 2011/0169960 A1* | 7/2011 | Wagner | 348/162 |

FOREIGN PATENT DOCUMENTS

| | | |
|---|---|---|
| EP | 1605526 | 5/2005 |
| WO | WO9852465 | 11/1998 |
| WO | WO03052444 | 6/2003 |
| WO | WO03075771 | 9/2003 |
| WO | WO2004068603 | 8/2004 |
| WO | WO2005030330 | 4/2005 |

(Continued)

OTHER PUBLICATIONS

"Quantum Efficiency and Linearity of 16 Phosphors in the Soft-X-Ray Regime", by D.E. Husk, et al., J. Opt. Soc. Am. B/vol. 9, No. 5/May 1992, pp. 660-663.

(Continued)

*Primary Examiner* — Tse Chen
*Assistant Examiner* — Amanda Lauritzen

(57) ABSTRACT

A therapeutic system includes a therapy module to direct a therapeutic action, e.g. focused ultrasound or RF energy to a target. An imaging module, such as a magnetic resonance examination system, generates image information of a therapy region that includes the target. By way of a motion analysis module, a motion vector field is derived from the image information of the therapy region. A control module controls the therapy module based on the motion vector field. For example, based on t the motion vector field, an accurate temperature distribution is derived from magnetic resonance signals and the motion vector field. Also magnetic resonance elastography data may be employed to improve the accuracy of the temperature distribution.

8 Claims, 2 Drawing Sheets

FOREIGN PATENT DOCUMENTS

| | | |
|---|---|---|
| WO | WO2006039009 | 4/2006 |
| WO | WO2007045075 | 4/2007 |
| WO | WO2008026134 | 3/2008 |

OTHER PUBLICATIONS

"VUV-Extended Measurements of Quantum Efficiency of Sodium Salicylate and of Some NBS Standard Phosphors", by Bernard Moine, et al., Optical Materials, 29 (2007) pp. 1148-1152.

"Imaging Anisotropic and Viscous Properties of Breast Tissue by Magnetic Resonance Elastography", by R. Sinkus, et al., in Magn. Reson. Med. 53 (2005372-387), [2005].

"Viscoelastic Shear Properties of In Vivo Breast Lesions Measured by MR Elastography", in Magn. Reson. Med. 23 (2005) 159-165, by R. Sinkus et al.

"Local Hyperthermia with MR-Guided Focused Ultrasound: Spiral Trajectory for the Focal Point Optimized for Temperature Uniformity in the Target Region", by R. Salomir, et al., in J. Magn. Res. IM. 12 (2000) 571-583.

"Ablation of Liver Tumors Using Percutaneous RF", by S.Nahum Goldberg, et al., Am J Roentgenol, Apr. 1998; 170 (4):1023-8.

* cited by examiner

IMAGE GUIDED THERAPY

FIELD OF THE INVENTION

The invention pertains to a therapeutic system comprising a therapy module to direct a therapeutic action to a target. The therapeutic system also comprises an imaging module to generate image information of a therapy region that includes the target and an area or volume around the actual target.

BACKGROUND OF THE INVENTION

Such a therapeutic system is known from the international application WO98/52465.

In the known therapeutic system the therapy module is an energy applicator such as a high intensity focused ultrasound unit. A magnetic resonance instrument has the function of the imaging module and is used to monitor hyperthermia treatments by the energy applicator. Further, the cited international application mentions that markers on the subject may be tracked so as to track and compensate for movement of the subject.

SUMMARY OF THE INVENTION

An object of the invention is to provide a therapeutic system which is able to take movements of the subject to be treated more accurately into account.

This object is achieved by a therapeutic system according to the invention comprising a motion analysis module to derive a motion vector field from the image information of the therapy region and a control module to control the therapy module on the basis of the motion vector field.

An insight on which the present invention is based, is that tracking of markers on the patient's skin only represents bulk movements of a therapy region that includes the target to be treated and consequently the control of the therapeutic action is not accurate. According to the invention a motion vector field represents local vector (magnitude and direction) movements of the therapeutic region at a predetermined spatial resolution. This motion vector field is employed to control the therapeutic action. This allows the therapeutic action to be more accurately directed to the actual target. The therapeutic action may e.g. be a high intensity focused ultrasound beam which generates heat in the focus at which it is directed and thus causes therapeutic effects such as local hyperthermia in the tissue at the focus. In another example the therapeutic action is performed by high intensity radio-frequent electromagnetic radiation that is directed to the target and causes RF or laser ablation of the tissue in the target. Also a device for cryo-ablation is possible, in which the tissue is ablated by lowering the temperature. Further, the therapeutic action may concern local gene transfection or drug release e.g. by locally elevated temperature or drug release by cavitation of micro-bubbles containing drugs as an adjuvant therapy.

The target is usually a local lesion such as a (cancerous) tumour or (uterine) fibroids or an area of the myocardium having abnormal electrical conduction. The therapy region is an area or a volume onto which the therapeutic action is directed and that includes the actual target. Often the therapy region is a well delimited portion of the patient's anatomy such as an organ (e.g. liver, uterus or heart).

Further, the therapeutic action can be controlled to avoid (a) selected portion(s) of the treatment region outside of the actual target. This is achieved in that the control module has the function to distinguish (a) portion(s) of the therapy region to be avoided. This can be done on the basis of information provided by the user e.g. on the basis of image information from the imaging module or on the basis of pre-acquired images. Then the therapeutic action is adjusted to avoid these distinguished portion(s).

Selected portions to be avoided by the therapeutic action may be parts of the anatomy that are sensitive to the therapeutic action (ultrasound or RF energy) but should not be damaged. The accurate control provided on the basis of the motion vector field allows accurate direction to actual target, such as the lesion, while avoiding unintentional damage to healthy tissue around the lesion.

In one aspect of the invention the motion vector field represents displacements, orientation and deformations of the therapy region. That is, the motion vector field represents changes in shape and size as well as local deformations. Thus the control on the basis of the motion vector field enables that the therapeutic action accounts for complicated movements and deformations of the therapy region. According to this aspect of the invention, markers are placed in the therapy region. These markers in the therapy region are imaged by the imaging module. For example the markers may be passive markers such as small spheres comprising a material having a short magnetisation decay time ($T_1$) which show up as signal voids in a magnetic resonance image, or as small spheres containing a material with another MR-observable nucleus, such as $^{19}F$, which can be imaged at a different frequency and without background noise (since this nucleus does not naturally occur in human bodies). Active markers may be used e.g. in the form of micro coils that emit an RF signal that is picked up by the magnetic resonance examination system and are represented in the magnetic resonance image. Either active and/or passive markers or a combination of active and passive markers can be employed. In particular these passive or active markers may be disposed on an invasive instrument, such as a catheter, guidewire or needle.

In another aspect of the invention the imaging module is formed by a magnetic resonance examination system which is arranged to perform thermography. That is, the magnetic resonance examination system generates and acquires magnetic resonance signals from the patient and derives a temperature distribution of the therapy region from the magnetic resonance signals. The motion vector field is derived on the basis of the representation of the markers. The markers are e.g. represented by magnetic resonance signals from the markers when active markers are used or by effects in the magnetic resonance signals caused by the markers when passive markers are used. In this embodiment a temperature distribution calculation module is provided which makes use of the motion vector field to calculate an accurate temperature distribution from the MR signal, taking phase effects of motion into account. On the basis of the motion vector field phase contributions to the magnetic resonance signals due to motion are isolated from phase contributions due to temperature. Hence, an accurate temperature distribution in which errors due to motion are avoided or corrected for on the basis of the motion vector field is derived from the magnetic resonance signals by means of the motion vector field.

In a further aspect of the invention the imaging module has the function to perform magnetic resonance elastography (MRE). The technique of MRE is known per se from the papers 'Imaging anisotropic and viscous properties of breast tissue by magnetic resonance elastography in Magn. Reson. Med. 53(2005372-387 and 'Viscoelastic shear properties of in vivo breast lesions measured by MR elastography' in Magn. Reson. Med. 23(2005)159-165 by R. Sinkus et al. The MRE imaging module produces maps of elasticity and viscous properties of the tissue of the therapy region. On the basis of these elasticity and/or viscosity properties and the representations of the markers in the image (e.g. magnetic resonance image) a highly accurate motion vector field is derived. The elasticity and/or viscosity properties allow to more accurately estimate the motion vector field at positions between the actually measured markers. For example, interpolation of the local movement, orientation and/or deformation at positions between the markers is interpolated on the basis of changes of positions of the markers where the interpolation is weighted on the basis of the elasticity and/or viscosity properties. Likewise, estimates of motion vectors can be obtained outside the region defined by the markers by extrapolation. Notably, as the tissue is more elastic, positions between the markers will follow the change of positions of the markers to a lesser extent and the tissue will be more deformed than displaced. The position of the passive or active markers are obtained by way of a conventional magnetic resonance imaging technique e.g. on the basis of magnetic resonance signals due to the markers. Further, the elasticity and/or viscosity properties acquired by MR elastography can be taken into account in the derivation of the temperature distribution of the therapy region. In this way deformation of the tissue is taken more accurately into account so that the temperature distribution is more accurate. Such highly accurate temperature distribution enables e.g. to trigger a genetic reaction or a drug release action in the target.

Another embodiment relates to a computer program. The computer program can be provided on a data carrier such as a CD-rom disk or a USB memory stick, or the computer program can be downloaded from a data network such as the world-wide web. When installed in the computer included in therapeutic system e.g. including a magnetic resonance imaging system, the therapeutic system of the invention is enabled to operate according to the invention and achieve a more accurate performance of the therapeutic action.

The invention also relates to a method of monitoring a therapeutic action. This method of monitoring a therapeutic action of the invention achieves a more accurate performance of the therapeutic action. The method of the invention merely provides monitoring information which forms a technical tool to support the physician in charge in carrying out the actual therapeutic action. Further, as only monitoring information is supplied concerning motion and/or deformation of the therapy region, the method of the invention in itself does not produce a diagnosis, or more in particular a diagnosis in stricto sensu, but rather produces an intermediate technical result of providing a technical aid to monitor the action of the therapy system.

BRIEF DESCRIPTION OF THE DRAWINGS

These and other aspects of the invention will be elucidated with reference to the embodiments described hereinafter and with reference to the accompanying drawing wherein.

DETAILED DESCRIPTION OF THE PREFERRED EMBODIMENTS

Figure 1:
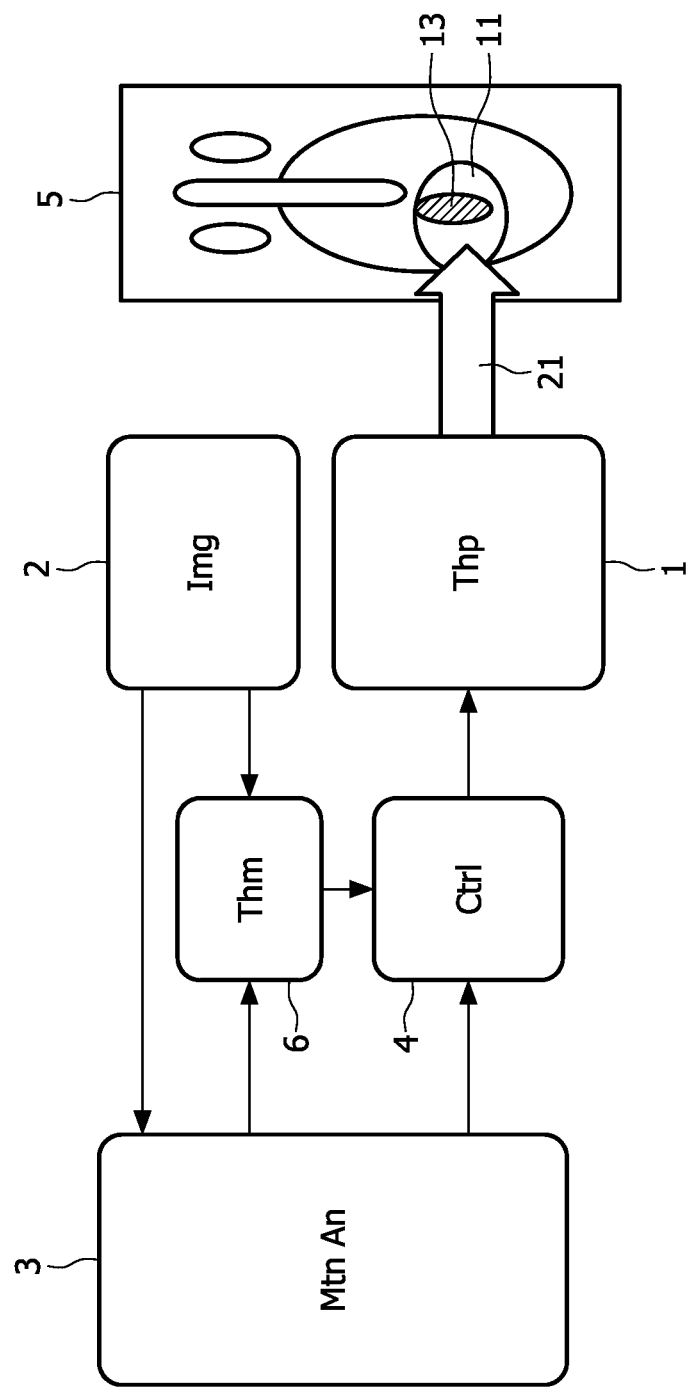
FIG. 1 shows a diagrammatic representation of a therapeutic system according to the invention and FIG. 2 shows a diagrammatic representation of the use of the motion vector field in a therapeutic system of the invention.

FIG. 1 shows a diagrammatic representation of a therapeutic system according to the invention. The therapeutic system comprises a therapy module 1 which applies a therapeutic action 21 to a target 13 in a therapy region 1 of a patient 5. For example the therapy module is a high-intensity focused ultrasound apparatus which focuses a high-intensity ultrasound beam onto the target 13 e.g. a uterine fibroid. Such a high-intensity ultrasound apparatus is known as such from the paper 'Local hyperthermia with MR-guided focused ultrasound: spiral trajectory for the focal point optimized for temperature uniformity in the target region' by R. Salomir et al. in J. Magn. Res. Im. 12(2000)571-583. Further, such a high-intensity ultrasound apparatus of which the ultrasound transducer can be easily directed to the target is described in the European patent application EP06119781.0. The therapy module can also be formed by an RF or laser ablation apparatus which deposits electromagnetic energy at the target, e.g. at a lesion in the myocardium. RF ablation as such is discussed in the paper *Am J Roentgenol*. 1998 Apr; 170(4):1023-8. The therapy module is controlled by a control module 4, notably the control module controls the position, direction and/or focusing of the therapeutic action such as the focused ultrasound beam or the RF energy beam.

The therapy system further comprises an imaging module 2, for example a magnetic resonance examination system. In particular the magnetic resonance examination system is enabled to perform magnetic resonance elastography. Alternatively, the imaging module can be any medical diagnostic imaging modality such as x-ray imaging, computed tomography or ultrasound imaging. The imaging module acquires image information from the patient 5, notably of the therapy region 11 e.g. in the form of magnetic resonance signals from which a magnetic resonance image can be reconstructed. When magnetic resonance elastography is employed the magnetic resonance elastography image represents local visco-elasticity properties of the therapy region. When in addition to a suitable magnetic resonance imaging protocol is employed for obtaining anatomical (morphological) information, the magnetic resonance signals may also represent the local temperature and thus the spatial temperature distribution of the therapy region can be derived. That is, the magnetic resonance examination system is also able to perform real-time thermography and—based on the measured temperature distribution—control the therapeutic action e.g. in the form of causing elevated local temperature in the tissue by means of suitably adjusting the therapy module. Further, the motion vector field derived on the basis of the local markers can be used to correct the local temperature for phase errors due to motion in the magnetic resonance signals. This is carried out in the temperature distribution module 6 that is arranged, notably in software, to compute the spatial temperature distribution in the therapy region on the basis of the magnetic resonance signals from the magnetic resonance examination system 2 and the motion vector field derived from the markers and/or visco-elastic properties.

Preferably, (shown in FIG. 2), local markers 12 are provided in or near the therapy region. A motion analysis module 3 is provided in the form of an image processing unit that is programmed to derive information about motion and deformation of the therapy region from a time series of images from the imaging module. From the image information the motion analyses module 3 derives the magnitude and local motion in the form of the motion vector field in the therapy region. In particular, the motion vector field is derived from the changes in position of the local markers in combination with the visco-elastic properties obtained from the magnetic resonance elastography data or from an organ model represented by a software program. The motion vector field is applied to the control module 4 which then (re-) adjusts the therapy module to direct the therapeutic action to the target and in this the movement and deformation of the target and/or the therapy region around the actual target is taken into account.

Figure 2:
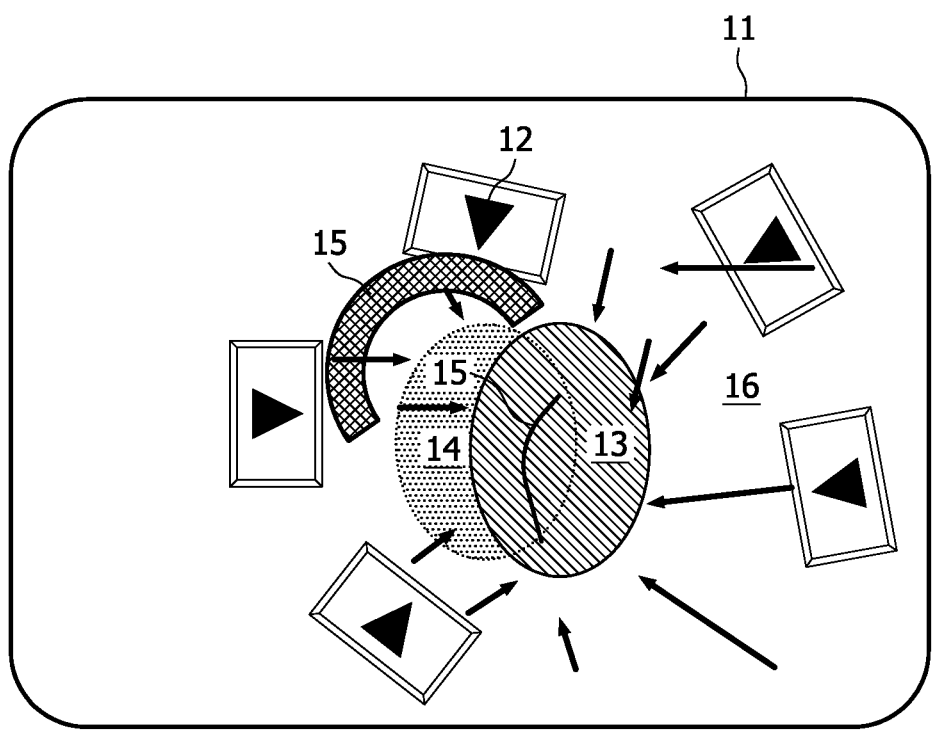

FIG. 2 shows a diagrammatic representation of the use of the motion vector field in a therapeutic system of the invention. In the therapy region 11 a target 13 is present. E.g. the therapy region is an organ such as the patient's heart or prostate or uterus to be treated and the target is a lesion, such as an electrical conduction fault in the patient's myocardium or a tumour or a uterine fibroid. From the change in position of the markers 12 and e.g. visco-elastic properties derived from magnetic resonance signals (or an organ model) the motion vector field 16 is computed. For example the motion vector field is computed by interpolation between measured displacements of the markers 12. In the interpolation the visco-elastic properties are taken into account in the interpolation coefficients. On the basis of the motion vector field the displacement and deformation and/or compression of the target is computed as represented by the displaced and deformed target 14. Also gross changes in shape inside the target may occur as indicated by the dent 15. Accordingly the therapeutic action is accurately directed onto the deformed and displaced target. Additionally, due account can be taken of healthy tissue delineated by the zone 15 that should be avoided by the therapeutic action 21.

The invention claimed is:

1. A therapeutic system comprising:
a therapy transducer configured to direct a therapeutic action to a target;
a magnetic resonance (MR) imager configured to generate image information of a therapy region that includes the target;
a motion analysis processor configured to derive a motion vector field from the image information of the therapy region; and
a controller configured to control the therapy transducer based on the motion vector field,
wherein the MR imager is configured to acquire MR signals from the therapy region, and to derive the image information from the magnetic resonance signals; and
wherein the controller includes a thermography unit configured to derive a temperature distribution of the therapy region from the magnetic resonance signals, taking the motion vector field into account.

2. The therapeutic system as claimed in claim 1, wherein the motion analysis processor is further configured to derive the motion vector field from representations of markers disposed on an invasive instrument in the therapy region.

3. The therapeutic system as claimed in claim 1, wherein the motion vector field represents at least one of displacement, orientation, and deformation of the therapy region.

4. The therapeutic system as claimed in claim 1 wherein the controller is further configured to:
distinguish at least a portion of the therapy region to be avoided; and
adjust the therapeutic action based on information about at least one of target motion and deformation such that the therapeutic action remains locally restricted to the target and avoids the distinguished portion.

5. The therapeutic system as claimed in claim 1 wherein the MR imager is formed by a magnetic resonance system configured to perform MR elastography, in order to derive image information representing visco-elasticity properties of tissue of the therapy region, and wherein the thermography unit is configured to take the visco-elastic properties into account in a temperature distribution of the therapy region.

6. A therapeutic system comprising:
a therapy transducer configured to direct a therapeutic action to a target;
a magnetic resonance (MR) imager configured to generate image information of a therapy region that includes the target;
a motion analysis processor to derive a motion vector field from the image information of the therapy region; and
a controller configured to control the therapy transducer based on the motion vector field,
wherein the MR imager is configured to perform MR elastography to derive image information representing visco-elasticity properties of tissue of the therapy region; and
wherein the motion analysis processor is further configured to derive the motion vector field also based on the visco-elasticity properties.

7. A non-transitory computer readable medium comprising computer instructions which, when executed by a processor, configure the processor to:
direct a therapeutic action to a target;
generate image information of a therapy region that includes the target;
derive a motion vector field from the image information of the therapy region;
control a therapy based on the motion vector field; and
derive a temperature distribution of the therapy region from the image information, taking the motion vector field into account.

8. A method to monitor a therapeutic action comprising the acts of:
generating, with a magnetic resonance (MR) imager, image information of a therapy region that includes the target;
deriving by a processor a motion vector field from the image information of the therapy region;
monitoring by a processor the therapeutic action based on the motion vector field; and
monitoring by a processor therapeutic action based on a temperature distribution which is calculated taking the motion vector field into account.

* * * * *